United States Patent
Nagai et al.

(10) Patent No.: US 7,998,079 B2
(45) Date of Patent: Aug. 16, 2011

(54) BIOSENSOR, SLEEP INFORMATION PROCESSING METHOD AND APPARATUS, COMPUTER PROGRAM THEREOF AND COMPUTER READABLE STORAGE MEDIUM THEREOF

(75) Inventors: Fumiya Nagai, Anjo (JP); Katsuyoshi Nishii, Okazaki (JP); Kazuhiro Sakai, Anjo (JP)

(73) Assignee: DENSO CORPORATION, Kariya (JP)

( * ) Notice: Subject to any disclaimer, the term of this patent is extended or adjusted under 35 U.S.C. 154(b) by 1513 days.

(21) Appl. No.: 11/410,079

(22) Filed: Apr. 25, 2006

(65) Prior Publication Data

US 2006/0241359 A1    Oct. 26, 2006

(30) Foreign Application Priority Data

Apr. 25, 2005    (JP) ................. 2005-126497

(51) Int. Cl.
*A61B 5/02* (2006.01)
(52) U.S. Cl. ............... 600/500; 600/301; 600/481
(58) Field of Classification Search ............ 600/301, 600/481, 500–508
See application file for complete search history.

(56) References Cited

U.S. PATENT DOCUMENTS

| | | | | |
|---|---|---|---|---|
| 5,101,831 A | * | 4/1992 | Koyama et al. | 600/500 |
| 6,856,829 B2 | * | 2/2005 | Ohsaki et al. | 600/479 |
| 2001/0032249 A1 | | 10/2001 | Worch | |
| 2003/0004423 A1 | * | 1/2003 | Lavie et al. | 600/500 |
| 2004/0049132 A1 | | 3/2004 | Barron et al. | |
| 2004/0162499 A1 | * | 8/2004 | Nagai et al. | 600/529 |
| 2004/0230398 A1 | | 11/2004 | Okada et al. | |
| 2005/0075553 A1 | * | 4/2005 | Sakai et al. | 600/372 |
| 2005/0234314 A1 | * | 10/2005 | Suzuki et al. | 600/301 |
| 2006/0189855 A1 | * | 8/2006 | Moriya et al. | 600/301 |
| 2008/0027331 A1 | * | 1/2008 | Suzuki et al. | 600/483 |
| 2008/0234785 A1 | * | 9/2008 | Nakayama et al. | 607/62 |

FOREIGN PATENT DOCUMENTS

| | | |
|---|---|---|
| JP | 04-109960 A | 4/1992 |
| JP | 2002-291710 | 10/2002 |
| JP | A-2003-216734 | 7/2003 |
| JP | 2004-113329 A | 4/2004 |
| JP | 2005-34402 A | 2/2005 |
| WO | WO 2004/107978 | 12/2004 |

OTHER PUBLICATIONS

Notice of Rejection mailed on Jun. 8, 2010 issued from the Japanese Patent Office in the corresponding Japanese patent application No. 2005-126497 (with English translation).

* cited by examiner

*Primary Examiner* — Charles A Marmor, II
*Assistant Examiner* — Karen E Toth
(74) *Attorney, Agent, or Firm* — Posz Law Group, PLC (57) ABSTRACT

A biosensor senses pulse wave data of a user. The biosensor stores relation information, which indicates a relationship between recommended bedtime data and sleep-affecting activity data. The relationship between the recommended bedtime data and the sleep-affecting activity data is determined in view of at least one of previously sensed pulse wave data of the user and model pulse wave data. The biosensor receives at least one sleep-affecting activity value from the user. The biosensor computes recommended bedtime information based on the at least one sleep-affecting activity value in view of the relation information. The biosensor gives notification to the user based on the recommended bedtime information.

21 Claims, 6 Drawing Sheets

BIOSENSOR, SLEEP INFORMATION PROCESSING METHOD AND APPARATUS, COMPUTER PROGRAM THEREOF AND COMPUTER READABLE STORAGE MEDIUM THEREOF

CROSS REFERENCE TO RELATED APPLICATION

This application is based on and incorporates herein by reference Japanese Patent Application No. 2005-126497 filed on Apr. 25, 2005.

BACKGROUND OF THE INVENTION

1. Field of the Invention

The present invention relates to a biosensor, sleep information processing method and apparatus, a computer program thereof and a computer readable storage medium thereof for evaluating a sleep condition and for counseling sleep condition improvement.

2. Description of Related Art

Conventionally, the Japanese Unexamined Patent Publication No. 2003-216734 discloses a technology for evaluating a sleep condition and for counseling sleep condition improvement.

This technology evaluates a daily sleep condition of a user and counsels the user to improve the sleep condition when the user accesses a specific website on the Internet and answers multiple questions. However, in the above-described technology, where the user inputs answers for a predetermined data (questionnaire), the technology may not provide a proper counseling output to the user because the technology depends on subjective inputs supplied by the user.

Further, because the sleep relates to a state, where the user is unconscious, it is difficult for the user to properly answer questions about the sleep.

SUMMARY OF THE INVENTION

It is therefore an object of the present invention to provide a biosensor, sleep information processing method and apparatus, a computer program thereof and a computer readable storage medium thereof, which obviates or mitigates at least one of the above disadvantages.

To achieve the objective of the present invention, there is provided a biosensor that includes a sensing means, a storage means, an input means, a bedtime computing means and a notifying means. The sensing means senses pulse wave data of a user. The storage means stores relation information, which indicates a relationship between recommended bedtime data and sleep-affecting activity data. The sleep-affecting activity data indicates a degree of a life activity that affects sleep. The relationship between the recommended bedtime data and the sleep-affecting activity data is determined in view of at least one of previously sensed pulse wave data of the user, which is sensed through the sensing means before preparation of the relation information, and model pulse wave data. The input means receives at least one sleep-affecting activity value from the user. The bedtime computing means computes recommended bedtime information based on the at least one sleep-affecting activity value received from the user through the input means in view of the relation information stored in the storage means. The notifying means gives notification to the user based on the recommended bedtime information, which is computed by the bedtime computing means.

To achieve the objective of the present invention, there is also provided a sleep information processing method that inputs a normal pulse wave data through an input means and that estimates a recommended sleep-affecting activity data based on the normal pulse wave data and relation information stored in a storage means. Here, the relation information indicates a relationship between sleep-affecting activity data, which indicates a degree of a life activity that affects sleep, and corresponding pulse wave data.

To achieve the objective of the present invention, there is also provided a sleep information processing apparatus, which includes a storage means, an input means, a bedtime computing means and a notifying means. The storage means stores relation information, which indicates a relationship between recommended bedtime data and sleep-affecting activity data. The sleep-affecting activity data indicates a degree of a life activity that affects sleep. The relationship between the recommended bedtime data and the sleep-affecting activity data is determined in view of at least one of previously sensed pulse wave data of a user, which is sensed through a sensing means before preparation of the relation information, and model pulse wave data. The input means receives at least one sleep-affecting activity value from the user. The bedtime computing means computes recommended bedtime information based on the at least one sleep-affecting activity value received from the user through the input means in view of the relation information stored in the storage means. The notifying means gives notification to the user based on the recommended bedtime information.

To achieve the objective of the present invention, there is also provided a sleep information processing apparatus for evaluating a sleep feature of a user, the apparatus including a sensing means, a storage means, a sleep evaluating means and a notifying means. The sensing means senses pulse wave data of the user. The storage means stores at least one relation information set, which indicates a relationship between model pulse wave data and corresponding sleep feature data. Here, the corresponding sleep feature data indicates a corresponding predetermined sleep feature. The sleep evaluating means evaluates the corresponding predetermined sleep feature based on the sensed pulse wave data of the user and the at least one relation information set. The notifying means notifies evaluation result data to the user based on the evaluated corresponding predetermined sleep feature.

To achieve the objective of the present invention, there is also provided a computer program embodied on a computer readable medium for processing sleep information, the computer program including several code segments. The computer program stores relation information in a storage means, the relation information indicating a relationship between recommended bedtime data and sleep-affecting activity data. Here, the sleep-affecting activity data indicates a degree of a life activity that affects sleep. The relationship between the recommended bedtime data and the sleep-affecting activity data is determined in view of at least one of previously sensed pulse wave data of a user, which is sensed by use of a sensing means before preparation of the relation information, and model pulse wave data. The computer program obtains at least one sleep-affecting activity value from the user by use of an input means. The computer program computes recommended bedtime information based on the at least one sleep-affecting activity value received from the user in view of the relation information stored in the storage means. The computer program gives notification to the user based on the recommended bedtime information by use of a notifying means.

To achieve the objective of the present invention, there is also provided a computer readable storage medium, which includes the above described computer program.

To achieve the objective of the present invention, there is also provided a computer program embodied on a computer readable medium for processing sleep information, the computer program including several code segments. The computer program senses pulse wave data of the user by use of a sensing means. The computer program stores at least one relation information set in a storage means, the at least one relation information set indicating a relationship between model pulse wave data and corresponding sleep feature data. Here, the corresponding sleep feature data indicates a corresponding predetermined sleep feature. The computer program evaluates each corresponding predetermined sleep feature based on the sensed pulse wave data of the user and a corresponding one of the at least one relation information set. The computer program notifies evaluation result data to the user based on the evaluated corresponding predetermined sleep feature by use of a notifying means.

To achieve the objective of the present invention, there is also provided a computer readable storage medium, which includes the above-described computer program.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF THE INVENTION

First Embodiment

A sleep information processing apparatus in a first embodiment displays a recommended interval (recommended remaining time period) between a finish time of drinking alcohol and a recommended bedtime after consumption of the alcohol. The recommended interval is recommended to achieve high quality sleep. Here, the recommended interval is calculated based on alcohol related data, such as an amount of the consumed alcohol and an interval (remaining time period) between the finish time of drinking the alcohol and an actual bedtime.

Figure 1:
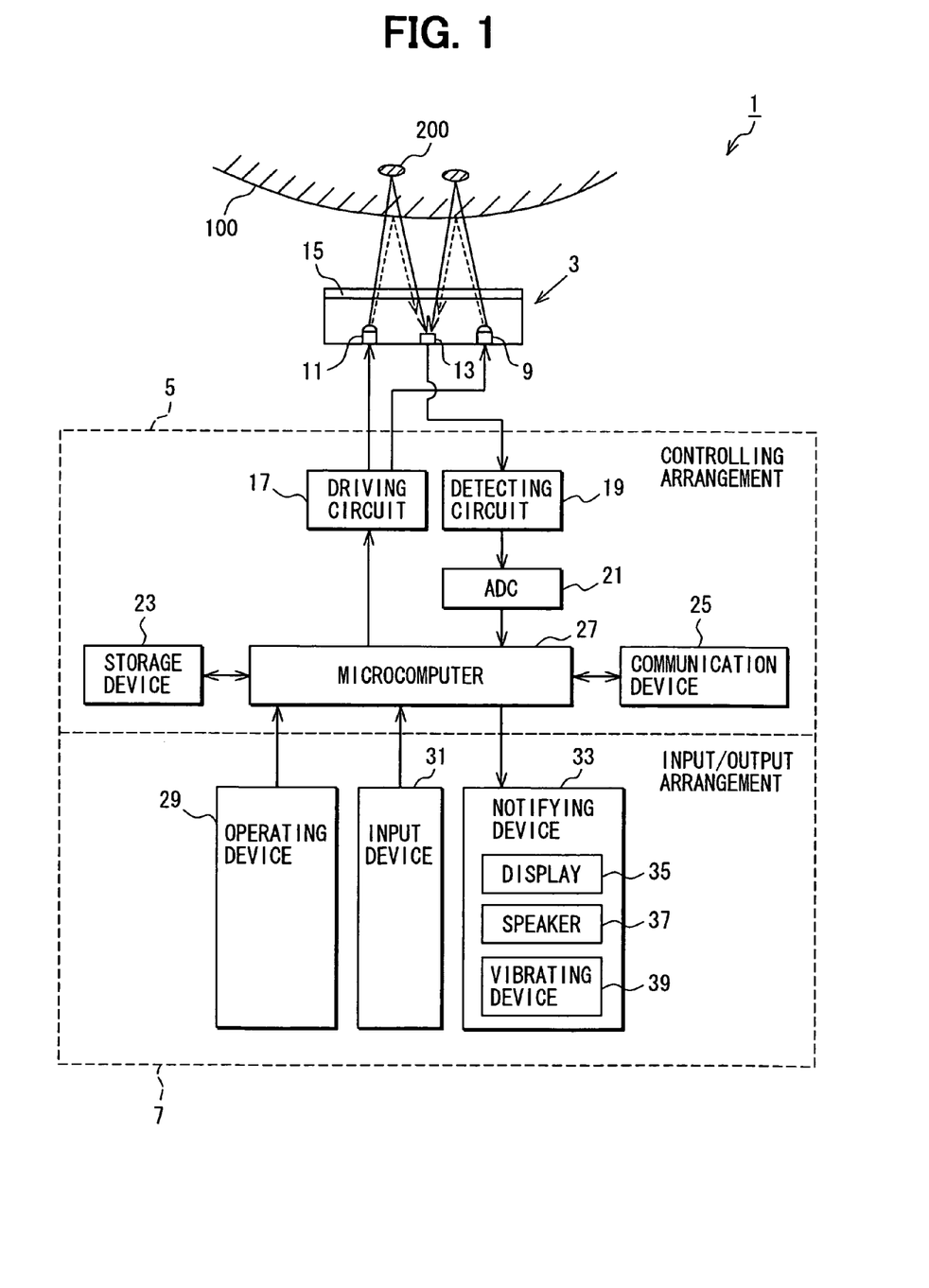
FIG. 1 is an explanatory diagram of a sleep information processing apparatus, which includes a pulse wave sensor according to a first embodiment.

The sleep information processing apparatus 1 is a mobile apparatus, which is mountable on an arm of a user, and includes a measuring arrangement 3, a controlling arrangement 5 and an input/output arrangement 7. The measuring arrangement 3 optically measures a pulse wave (pulse wave data). The controlling arrangement 5 processes data. The input/output arrangement 7 receives and outputs information.

The measuring arrangement 3 includes a pair of light emitting diodes (LEDs) 9, 11, a photo diode (PD) 13 and a transparent window 15. The pair of LEDs 9, 11 includes a green light emitting diode (green LED) 9 and an infrared light emitting diode (infrared LED) 11. The PD 13 receives reflecting lights of the pair of LEDs 9, 11.

The green LED 9 radiates a green light to a human body 100 for detecting the pulse wave based on the reflecting green light. Here, the reflecting green light associates with a variation of an amount of hemoglobin in capillary arteries 200. The infrared LED 11 radiates a infrared light to the human body 100 for detecting a body motion based on the reflecting infrared light.

The controlling arrangement 5 operates the measuring arrangement 3 and measures the pulse wave by processing signals supplied by the measuring arrangement 3. Also the controlling arrangement 5 analyzes the pulse wave to detect a parasympathetic nerve activity condition and analyzes a sleep condition (sleep quality).

The controlling arrangement 5 includes a driving circuit 17, a detecting circuit 19, an analog-digital converter (ADC) 21, a storage device 23, a communication device 25 and a microcomputer 27. The driving circuit 17 operates the LEDs 9, 11. The detecting circuit 19 receives analog signals supplied by the PD 13. The ADC 21 converts the analog signals to digital signals. The storage device 23 stores data. The communication device 25 is externally communicated. The microcomputer 27 controls the controlling arrangement 5.

The input/output arrangement 7 includes an operating device 29, an input device 31 and a notifying device 33. The operating device 29 turns on and off a power source. The input device 31 receives data, such as the finish time of drinking alcohol and the amount of the consumed alcohol. The notifying device 33 notifies the user of an analysis result and advices. The notifying device 33 includes a display 35, a speaker 37 and a vibrating device 39. The display 35 shows characters and images. The speaker 37 gives notification to the user by use of a sound. The vibrating device 39 gives the notification to the user by use of vibration.

A pulse sensor for optically detecting the pulse wave data includes the measuring arrangement 3, the driving circuit 17, the detecting device 19 and the microcomputer 27 in FIG. 1. Thus, the sleep information processing apparatus 1 in the first embodiment integrally includes the pulse-wave sensor. That is, the sleep information processing apparatus 1 serves as the pulse-wave sensor.

Next, a relation between the parasympathetic nerve activity condition and the interval between the finish time of drinking the alcohol and the bedtime will be described.

Figure 2A:
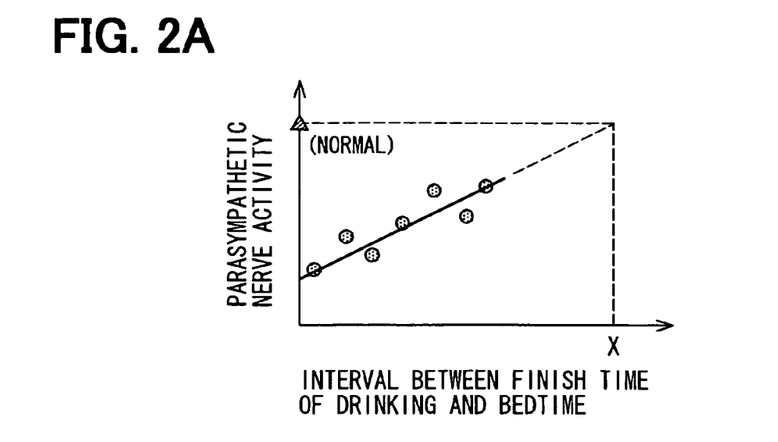
FIG. 2A is a graph showing data used for a process by the sleep information processing apparatus according to the first embodiment.

As shown in FIG. 2A, there is a relationship between the parasympathetic nerve activity at the bedtime and the interval between the finish time of drinking the alcohol and the bedtime. When the interval is large, the parasympathetic nerve activity at the bedtime becomes high.

Figure 3A:
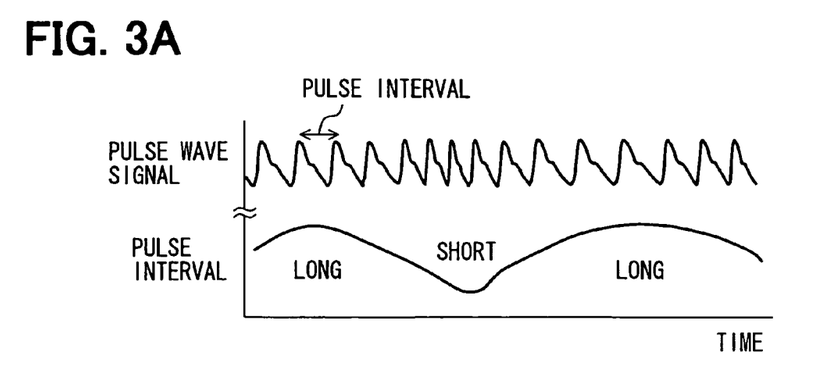
FIG. 3A is a diagram showing a pulse wave signal and a pulse wave interval according to the first embodiment.
Figure 3B:
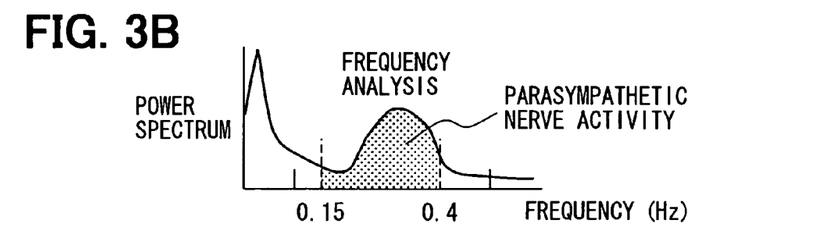
FIG. 3B is a diagram showing a power spectrum used in a frequency component analysis according to the first embodiment.

The parasympathetic nerve activity, which corresponds to high frequency component (HF) in FIG. 3B, indicates a degree of a rest (brake) of the human body. A sympathetic nerve activity, which corresponds to a low frequency component (LF) in FIG. 3B, indicates a degree of activeness (acceleration) of a human body activity in contrast to the parasympathetic nerve activity. Thus, as the parasympathetic nerve activity becomes high, the degree of the rest of the human body increases, and a sleep quality is improved (i.e., sufficiently sound sleep can be achieved).

The parasympathetic nerve activity condition can be known by, for example, a pulse wave as shown in FIGS. 3A and 3B (see Japanese Unexamined Patent Publication No. 2002-291710). Specifically, frequency components of fluctuation of a pulse interval are calculated based on the pulse interval, which is shown in FIG. 3A. Then, in a frequency components analysis in FIG. 3B, the parasympathetic nerve activity can be evaluated based on a power spectrum of a predetermined frequency band (e.g., 0.15 to 0.4 Hz). For example, when a peak value or an integral value of the power spectrum in the predetermined frequency band is large, the parasympathetic nerve activity is determined as high. This means that the sleep quality is determined as high.

Returning to the first embodiment of the present invention, the intervals between the finish times and the actual bedtimes and corresponding parasympathetic nerve activity values at the actual bedtimes are previously stored to serve as a basic parent population of measured data (base data). The corresponding parasympathetic nerve activity value indicates the corresponding parasympathetic nerve activity condition. The base data serves as relation information. For example, the sleep information processing apparatus 1 is turned on at the bedtime to measure the parasympathetic nerve activity value, and the interval between the finish time of drinking the alcohol and the bedtime is inputted to the sleep information processing apparatus 1 by the user. The sleep information processing apparatus 1 measures the corresponding parasympathetic nerve activity value (e.g., average value) for some minutes to some ten minutes from the bedtime. Then, these multiple individual data sets are stored as the base data. The user may store the base data for him/herself, however, base data of people of the same generation with the user or of the same gender with the user may be stored. Here, people of the same generation may be in their thirtysomethings if the user is 36 years old. Alternatively, a margin of an age difference between the user and the people with the same generation may be within five years.

FIG. 2A shows a graph of the base data. In the graph, an axis of ordinates indicates the parasympathetic nerve activity value (e.g., the integral value of the power spectrum) and an axis of abscissas axis indicates the interval between the finish time of drinking the alcohol and the bedtime.

An oblique line in the graph indicates an approximate line (relation equation) of the base data. A specific interval is calculated based on a normal parasympathetic nerve activity value, which corresponds to normal pulse wave data at a non alcohol-consuming time, and the approximate line of the base data. The specific interval serves as a recommended interval X between the finish time of drinking alcohol and the recommended bedtime. Here, the non alcohol-consuming time means a time where the user does not drink alcohol. After the recommended interval X, the alcohol may not affect the sleep quality of the user even after the user drinks. Therefore, when the recommended interval X is taken before the bedtime after the consumption of the alcohol, the alcohol may slightly affect the sleep quality or the alcohol may not affect the sleep quality.

Thus, based on the base data of the graph, the sleep information processing apparatus 1 can provide a recommended period (e.g. hours or minutes) to be waited before a bedtime for achieving the high quality sleep when, for example, a present time is inputted to the sleep information processing apparatus 1. Therefore, when the recommended bedtime has come, the sleep information processing apparatus 1 gives notification to the user so that the user can go to sleep to achieve the high quality sleep.

Figure 4:
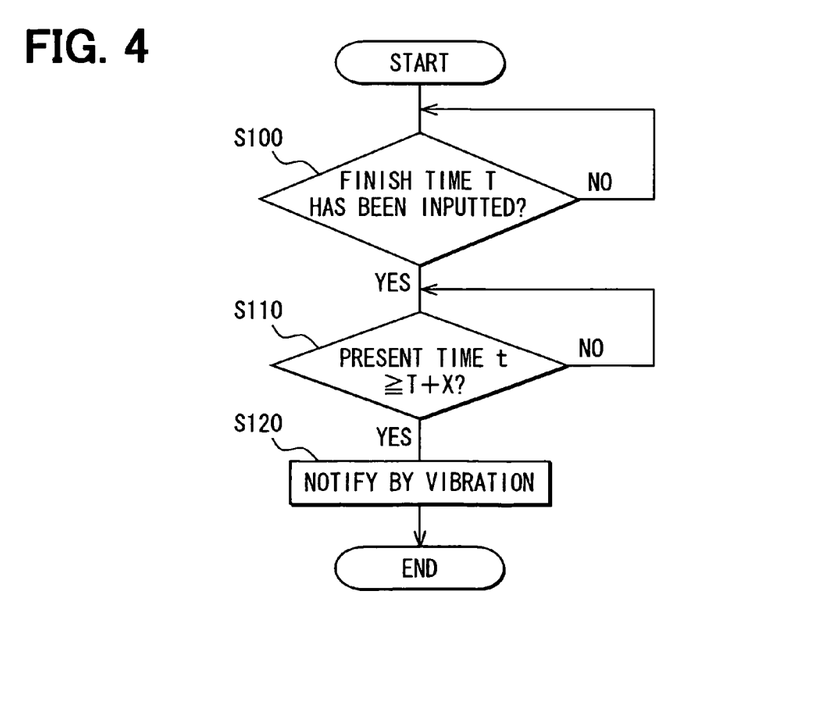
FIG. 4 is a flowchart of a control process of the sleep information processing apparatus according to the first embodiment.

Next, a process for notifying the recommended bedtime based on the base data will be described with reference to a flowchart in FIG. 4.

At step S100, it is determined whether a finish time T of drinking alcohol has been inputted. When the finish time T of drinking alcohol has been inputted, step S110 is executed. When the finish time T of drinking alcohol has not been inputted, step S100 is repeatedly executed.

At step S110, it is determined whether a present time t has reached a recommended bedtime, which is calculated by adding the recommended interval X to the finish time T. This means that it is determined whether the recommended interval X has passed since the user finished drinking the alcohol at the finish time T. When the recommended interval X has passed since the user finished drinking the alcohol at the finish time T, step S120 is executed. When the recommended interval X has not passed, step S110 is repeatedly executed.

At step S120, the sleep information processing apparatus 1 notifies the user by use of the vibrating device 39 that the recommended interval X has passed since the user finished drinking. After the user is so notified, the user may sleep so that the user can achieve the high quality sleep.

Next, a relationship between the parasympathetic nerve activity value and the amount of the consumed alcohol will be described.

Figure 2B:
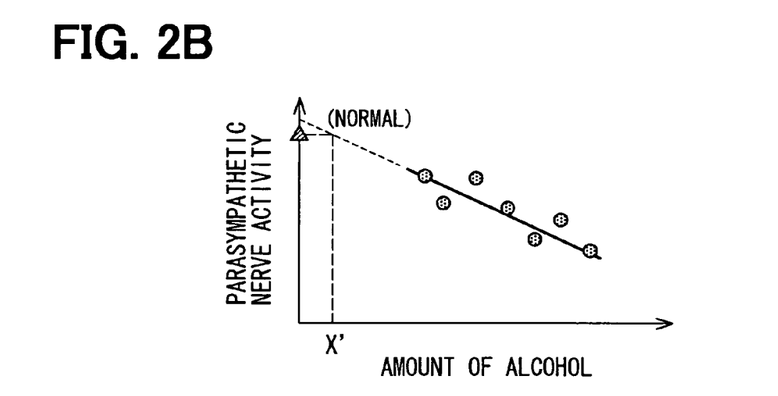
FIG. 2B is another graph showing data used for a process by the sleep information processing apparatus according to the first embodiment.

There is the relationship between the parasympathetic nerve activity value and the amount of the consumed alcohol as shown in FIG. 2B. When the amount of the consumed alcohol is small, the parasympathetic nerve activity becomes high and the high quality sleep may be achieved.

Specifically, an approximate line is made based on the base data, which indicate the relationship between the parasympathetic nerve activity and the amount of the consumed alcohol. A specific amount of the consumed alcohol is calculated based on the normal parasympathetic nerve activity value at the non alcohol-consuming time and the approximate line of the base data, which indicates the parasympathetic nerve activity and the amount of the consumed alcohol. The specific amount serves as a recommended amount X' of the consumed alcohol, which may not affect the sleep quality very much. Thus, when the user drinks the alcohol less than the recommended amount X', the sleep quality of the user may not be affected very much.

Next, a relationship among the parasympathetic nerve activity, the amount of the consumed alcohol and the interval between the finish time and the bedtime will be described with reference to FIG. 2C.

As described above, each of the interval and the amount of the consumed alcohol has the relationship with the corresponding parasympathetic nerve activity. Thus, both the interval and the amount of the consumed alcohol are incorporated into new data for an alternative graph shown in FIG. 2C.

Figure 2C:
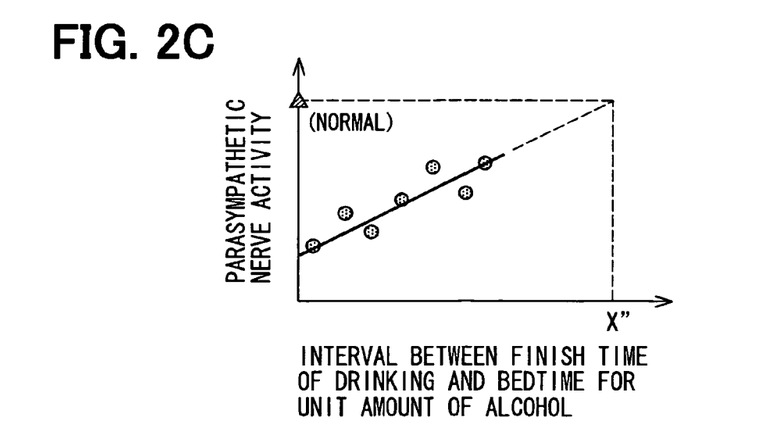
FIG. 2C is another graph showing data used for a process by the sleep information processing apparatus according to the first embodiment.

Specifically, in the graph in FIG. 2C, the axis of ordinates indicates the parasympathetic nerve activity value and the axis of abscissas indicates an interval for a unit amount of the consumed alcohol (i.e., the interval÷the amount of consumed alcohol).

Also, in this case, an approximate line is made based on the base data, which indicate relationship between the parasympathetic nerve activity and the interval for the unit amount of the consumed alcohol. A specific interval for the unit amount is calculated based on the normal parasympathetic nerve activity value at the non alcohol-consuming time and the approximate line of the base data. The specific interval serves as a recommended interval X" for the unit amount of the consumed alcohol, which may not affect the sleep quality very much.

Thus, the recommended interval between the finish time of drinking alcohol and the recommended bedtime can be calculated by multiplying the recommended interval X" by the amount of the consumed alcohol. After the recommended bedtime, the alcohol may not affect the sleep quality of the user very much.

Figure 5:
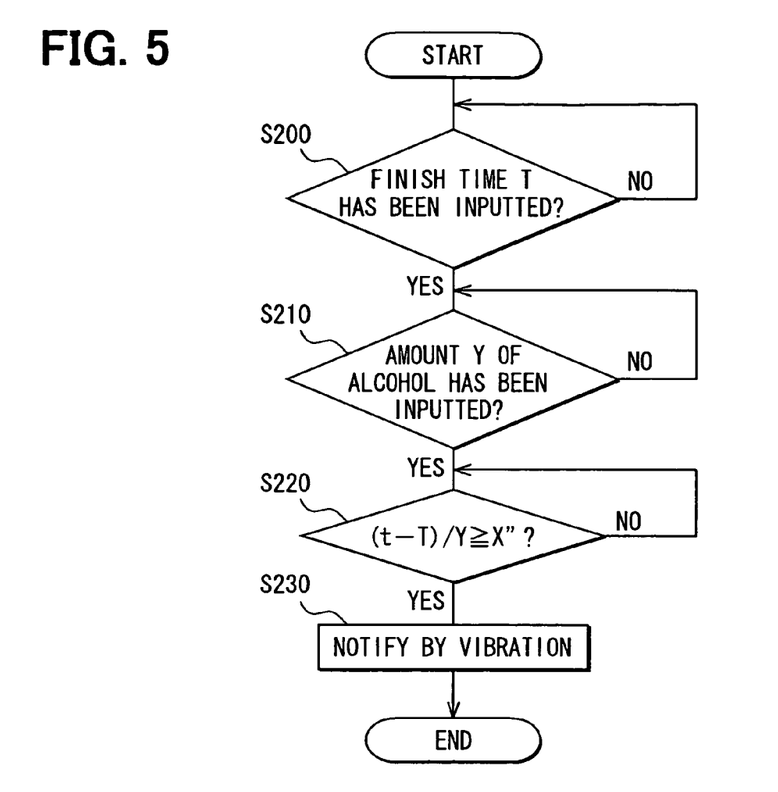
FIG. 5 is a flowchart of another control process of the sleep information processing apparatus according to the first embodiment.

Next, another process for notifying the recommended bedtime based on the base data will be described with reference to a flowchart in FIG. 5.

At step S200, it is determined whether the finish time T of drinking alcohol has been inputted to the sleep information processing apparatus 1. When the finish time T of drinking alcohol has been inputted, step S210 is executed. When the finish time T of drinking alcohol has not been inputted, step S200 is repeatedly executed.

At step S210, it is determined whether an amount Y of the consumed alcohol has been inputted to the apparatus 1. When the amount Y of the consumed alcohol has been inputted, step S220 is executed. When the amount Y of the consumed alcohol has not been inputted, step S210 is repeatedly executed.

At step S220, it is determined whether a calculated value $$\left(\frac{t-T}{Y}\right),$$

which is calculated through dividing a difference between the present time t and the finish time T of drinking alcohol by the amount Y, has reached the recommended interval X", which is the recommended interval for the unit amount of the consumed alcohol. This alternatively means that it is determined whether a specific interval, which is calculated by multiplying the recommended interval X" by the amount Y of the consumed alcohol, has elapsed since the user finished drinking the alcohol. When the calculated value $$\left(\frac{t-T}{Y}\right)$$

has reached the recommended interval X", step S230 is executed. When the calculated value $$\left(\frac{t-T}{Y}\right)$$

has not reached the recommended interval X", step S220 is repeatedly executed. In other words, the sleep information processing apparatus 1 gives the notification to the user at the recommended bedtime.

At step S230, by operating the vibrating device 39, the sleep information processing apparatus 1 notifies the user that the recommended interval has elapsed since the user finished drinking. After the user is so notified, the user may sleep so that the user can achieve the high quality sleep. Also, because the recommended bedtime is determined based on the amount Y and the finish time T of drinking alcohol, a higher degree of accuracy of the recommended bedtime can be achieved.

In the present embodiment, the recommended interval X, which indicates the recommended bedtime after the consumption of the alcohol, is calculated based on the statistical data of the relationship between the parasympathetic nerve activity and the interval between the finish time of drinking the alcohol and the actual bedtime (or of the relationship between the parasympathetic nerve activity and the amount of the consumed alcohol). Also the user is notified the recommended bedtime. Therefore, the user can achieve the high quality sleep because the user may not be affected by the alcohol very much at the recommended bedtime.

In the present embodiment, the recommended interval X, the recommended amount X' of the consumed alcohol and the recommended interval X" for the unit amount of the consumed alcohol are calculated based on the intervals and the amounts of the consumed alcohol. However, the recommended interval X, the recommended amount X' and the recommended interval X" may be alternatively calculated based on a relationship among an interval between a finish time of taking exercise and an actual bedtime, an amount of the exercise and a corresponding parasympathetic nerve activity. Then, the user may be notified of a recommended bedtime based on an alternative recommended interval X between the finish time of taking the exercise and the recommended bedtime, an alternative recommended amount X' of the exercise and an alternative recommended interval X" between the finish time of taking the exercise and the recommended bedtime for a unit amount of the exercise.

Also, in the present embodiment, the sleep information processing apparatus, which integrally includes the pulse wave sensor for sensing the pulse wave and the analyzing structure for analyzing the sleep condition, is described. However, the sleep information processing apparatus may be separated from the pulse wave sensor and the analyzing structure. The sleep information processing apparatus may be connected with the pulse wave sensor and the analyzing structure through wire or radio communication.

Second Embodiment

A second embodiment will be described. Similar components of a sleep information processing apparatus of the second embodiment, which are similar to the components of the sleep information processing apparatus of the first embodiment, will be indicated by the same numerals. Explanation, which is similar to the first embodiment, will be omitted.

In the second embodiment, an operation of the sleep information processing apparatus is different from that of the first embodiment. Thus, the operation will be described.

The sleep information processing apparatus 1 in the second embodiment measures human body condition, such as the pulse wave (pulse wave data), similarly to the first embodiment. Then, analysis results based on the measured data are shown in the display 35.

Figure 6:
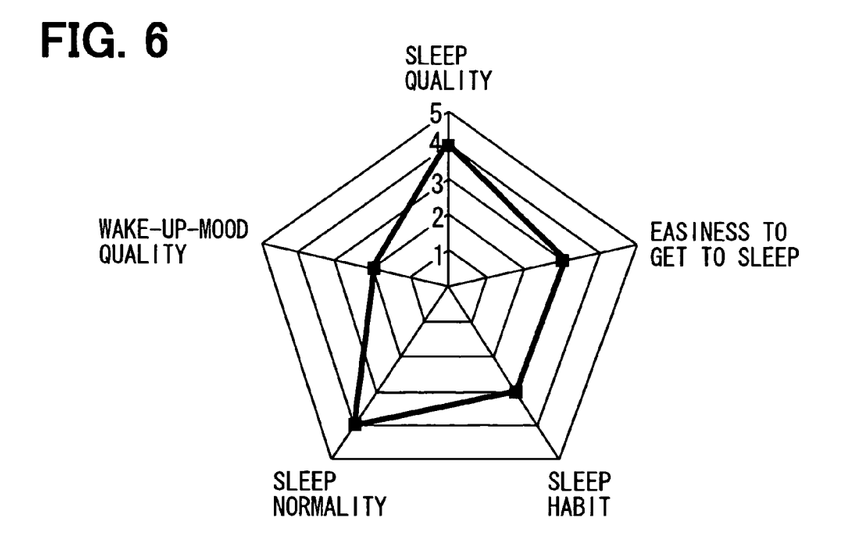
FIG. 6 is an explanatory diagram of a radar chart, which is shown in a display of a sleep information processing apparatus according to a second embodiment.

For example, five evaluation categories, such as the sleep quality, easiness to get to sleep, wake-up-mood quality, sleep habit and sleep normality, are evaluated by grades for analysis, and the analysis results are shown in a radar chart as shown in FIG. 6.

Next, an operation process in the second embodiment will be described.

Firstly, processes for measuring data and for calculating the evaluation categories will be described.

Figure 7:
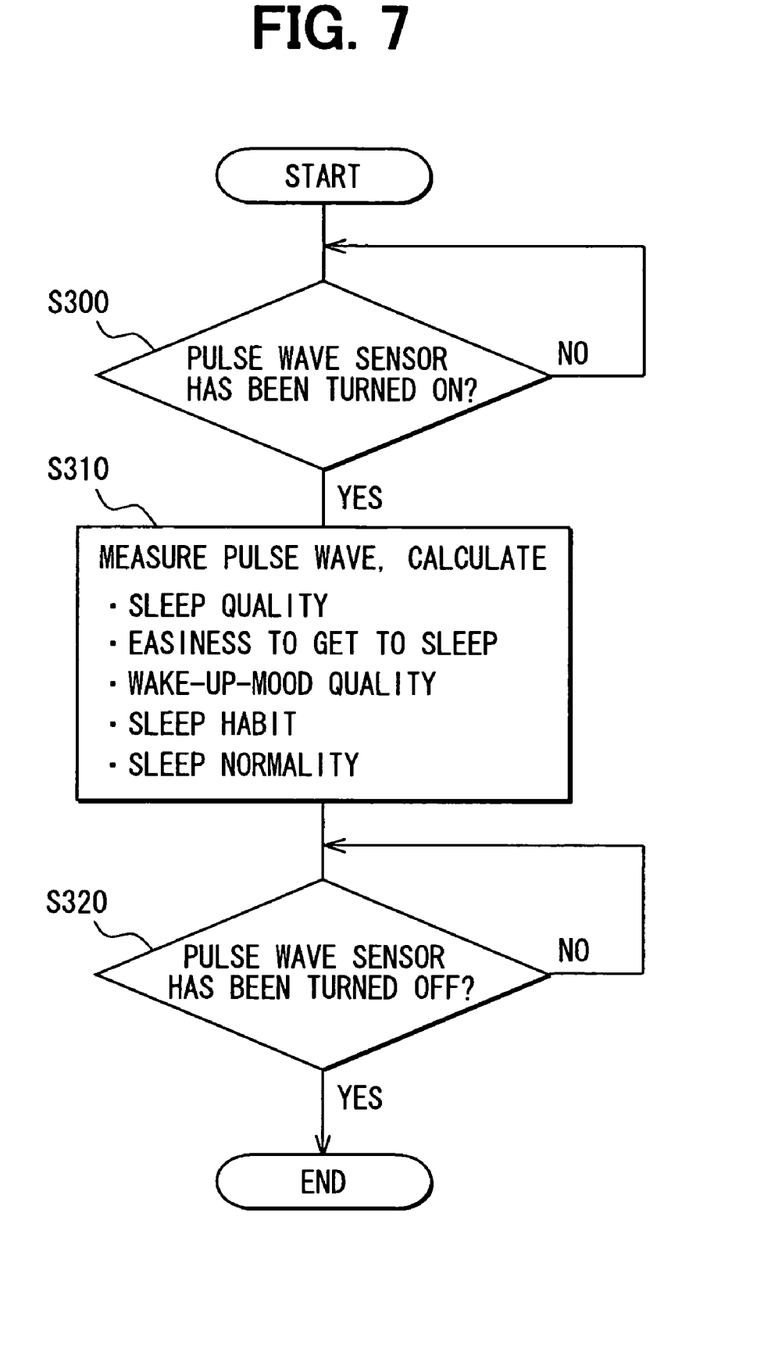
FIG. 7 is a flowchart of a control process of the sleep information processing apparatus according to the second embodiment.

As shown in FIG. 7, at step S300, the sleep information processing apparatus 1, which serves as the pulse wave sensor, determines whether a power switch (not illustrated) has been turned on. When the power switch has been turned on, step S310 is executed.

At step S310, the pulse wave is measured and simultaneously multiple calculations are performed for processing the measured data for the evaluation. Then, the measured data and calculation results are stored in the storage device (memory) 23.

Specifically, as described later, the calculations are performed to evaluate the sleep quality, the easiness to get to sleep, the wake-up-mood quality, the sleep habit and the sleep normality.

In the calculation of each of the evaluation categories, measured data for a predetermined period is required or a predetermined amount of measured data is required. Thus, this calculation process is repeated until the required amount of data is stored.

At step S320, it is determined whether the power switch has been turned off. When the power switch has been turned off, the present process is temporally ended. When the required amount of measured data for the calculation of each of the evaluation categories is stored, a value for each of the evaluation categories can be calculated.

Next, a process for displaying the calculation results of the evaluation categories will be described.

Figure 8:
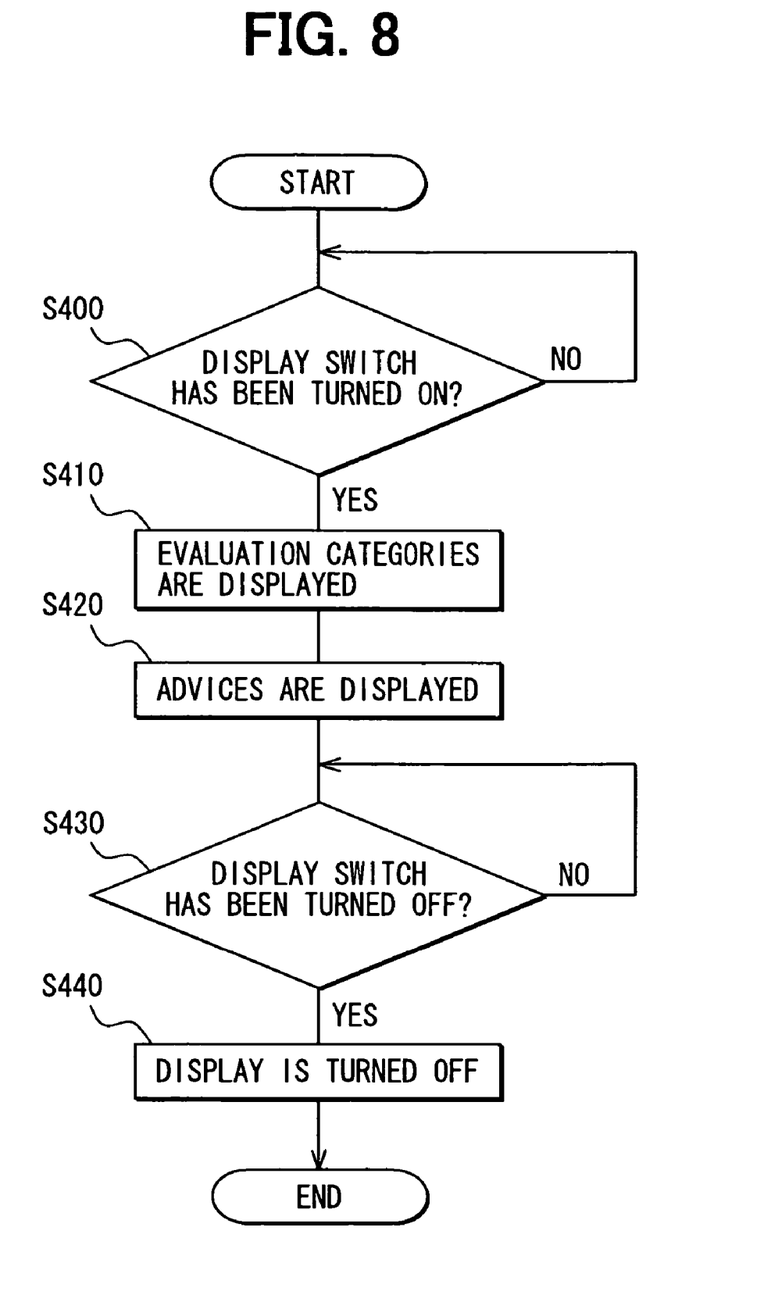
FIG. 8 is a flowchart of another control process of the sleep information processing apparatus according to the second embodiment.

As shown in FIG. 8, it is determined whether a display switch (not illustrated) has been turned on at step S400. When the display switch has been turned on, step S410 is executed.

At step S410, a calculated value for each of the evaluation categories stored in the storage device 23 is presented in the display 35 with a format of the radar chart as shown in FIG. 6.

At step S420, advices are presented based on the calculated value of each of the evaluation categories displayed in the radar chart. The advices are automatically calculated based on a predetermined corresponding algorithm, which corresponds to each of the evaluation categories, and shown in the display 35. Thus, the advices are calculated and stored in the storage device 23 simultaneously when each of the evaluation categories is calculated.

At step S430, it is determined whether the display switch has been turned off. When the display switch has been turned off, step S440 is executed.

At step S440, the values for the evaluation categories and the advices disappear from the display 35, and the present process is temporally turned off.

Thus, the calculated value for each of the evaluation categories and the corresponding advice can be provided at any time when needed.

In the present embodiment, the calculated value for each of the five evaluation categories is displayed, however, the calculated value for each of selected ones of the five evaluation categories may be alternatively displayed. Also, each of the evaluation categories may be weighed and a summary of each of weighed calculated values of the evaluation categories may be displayed as a total value.

Each of the above-described evaluation categories will be described in detail.

In evaluating the sleep quality as the evaluation category, an autonomic nerve activity, which is determined based on a heart rate variability analysis, is used. For example, at least one of an overnight accumulated value of parasympathetic nerve activity values during a non-rapid eye movement (NREM) sleep and an overnight average value of the parasympathetic nerve activity values is measured and calculated to serve as an indicator for the autonomic nerve activity. Here, the parasympathetic nerve activity value indicates a condition of the parasympathetic nerve activity. When the parasympathetic nerve activity values are large, it is determined that the sleep quality is high.

Japanese Unexamined Patent Publication No. 2002-291710 discloses calculation methods for the average value and the accumulated value of the parasympathetic nerve activity values. Specifically, frequency analysis is conducted to calculate fluctuation of the pulse interval. Then, frequency components in the frequency band of 0.15 to 0.45 Hz are obtained. The average value and the accumulated value of magnitudes (powers) of the frequency components therein indicate the average value and the accumulated value of the parasympathetic nerve activity values.

Returning to the second embodiment of the present invention, for example, the average value (A) of the parasympathetic nerve activity values are scored to evaluate the sleep quality. The average value (A) of the parasympathetic nerve activity values is scored based on an average comparative value (B) of prestored multiple average values of the parasympathetic nerve activity values stored in the storage device 23 as the base data. Here, the average comparative value (B) is an average of the prestored average values. The average value (A) is scored at a maximum point when the average value (A) is greater than "the average comparative value (B)+3$\sigma$". Also, the average value (A) is scored at a second highest point when the average value (A) is ranged between "the average comparative value (B)+2$\sigma$" and "the average comparative value (B)+3$\sigma$". The average value (A) is scored at a third highest point when the average value (A) is ranged between "the average comparative value (B)+$\sigma$" and "the average comparative value (B)+2$\sigma$". The average value (A) is scored less than the third highest point when the average value (A) is smaller than "the average comparative value (B)+$\sigma$". The accumulated value is scored similarly to the average value based on a corresponding accumulated comparative value, which is an average of prestored accumulated values. Each of the scores of the average value and the accumulated value is assigned a corresponding weight described as each coefficient W1 and W2 respectively.

Thus, the sleep quality is scored by use of an equation 1.

Score of Sleep Quality=$W1$×Score of Average Value of Parasympathetic Nerve Activity+$W2$×Score of Accumulated Value of Parasympathetic Nerve Activity  (Equation 1)

The overnight average value and accumulated value of the parasympathetic nerve activity are scored based on the prestored base data. The base data may alternatively be data of a particular user, data of people of the same generation with the user and data of people of the same gender with the user. These alternatives may be applied to any base data in the present invention.

The easiness to get to sleep is evaluated based on at least one of a hypnagogic heart rate, a variation rate of the hypnagogic heart rate (degree of decrease of the hypnagogic heart rate), a duration time of body motion and a hypnagogic parasympathetic nerve activity value, which indicates a parasympathetic nerve activity condition at the bedtime.

When the hypnagogic heart rate, which corresponds to a heart rate for a predetermined period after getting to sleep, is smaller, the easiness to get to sleep is determined to be better. Also, when the variation rate of the hypnagogic heart rate is smaller (the degree of decrease of the hypnagogic heart rate is larger), also when the duration time of body motion is shorter, also when the hypnagogic parasympathetic nerve activity value is larger, the easiness to get to sleep is determined to be better. The hypnagogic period corresponds to the predetermined period since the user gets to sleep. A well-known method can determine whether the user gets to sleep based on signals supplied by the pulse wave sensor. Also, the body motion can be detected based on noises supplied by electrocardiograph and also based on signals supplied by the infrared LED and an acceleration sensor (G sensor). An additional body motion sensor may be alternatively provided.

The hypnagogic heart rate is scored based on an average comparative value of prestored hypnagogic heart rates, which are stored in the storage device 23 as base data. The hypnagogic heart rate is scored at the maximum when the hypnagogic heart rate is smaller than "the average comparative value$-3\sigma$". Also, the hypnagogic heart rate is scored at the second highest point when the hypnagogic heart rate is ranged between "the average comparative value$-3\sigma$" and "the average comparative value$-2\sigma$". The hypnagogic heart rate is scored at the third highest point when the hypnagogic heart rate is ranged between "the average comparative value$-2\sigma$" and "the average comparative value$-\sigma$". The hypnagogic heart rate is scored less than the third highest point when the hypnagogic heart rate is larger than "the average comparative value$-\sigma$". The duration time of body motion is also scored similarly to the hypnagogic heart rate based on a corresponding average comparative value of prestored duration times of body motion.

The hypnagogic parasympathetic nerve activity value is scored based on an average comparative value of prestored hypnagogic parasympathetic nerve activity values, which are stored in the storage device 23 as the base data. The hypnagogic parasympathetic nerve activity value is scored at a maximum point when the hypnagogic parasympathetic nerve activity value is larger than "the average comparative value$+3\sigma$". Also, the hypnagogic parasympathetic nerve activity value is scored at the second highest point when the hypnagogic parasympathetic nerve activity value is ranged between "the average comparative value$+2\sigma$" and "the average comparative value$+3\sigma$". The hypnagogic parasympathetic nerve activity value is scored at the third highest point when the hypnagogic parasympathetic nerve activity value is ranged between "the average comparative value$+\sigma$" and "the average comparative value$+2\sigma$". The hypnagogic parasympathetic nerve activity value scored less than the third highest point when the hypnagogic parasympathetic nerve activity value is smaller than "the average comparative value$+\sigma$".

The variation rate of the hypnagogic heart rate is scored based on an average comparative value of prestored degrees of decrease of the hypnagogic heart rate in the following two cases. In the first case, where the heart rate is smaller than a predetermined value, the variation rate of the hypnagogic heart rate is scored at the maximum when the variation rate of the hypnagogic heart rate is smaller than "the average comparative value$-3\sigma$". Also, the variation rate of the hypnagogic heart rate is scored at the second highest point when the variation rate of the hypnagogic heart rate is ranged between "the average comparative value$-3\sigma$" and "the average comparative value$-2\sigma$". The variation rate of the hypnagogic heart rate is scored at the third highest point when the variation rate of the hypnagogic heart rate is ranged between "the average comparative value$-2\sigma$" and "the average comparative value$-\sigma$". The variation rate of the hypnagogic heart rate is scored less than the third highest point when the hypnagogic heart rate is larger than "the average comparative value$-\sigma$".

In the second case, where the heart rate is larger than the predetermined value, the variation rate of the hypnagogic heart rate is scored as zero when the variation rate of the hypnagogic heart rate is larger than "the average comparative value$+3\sigma$". Also, the variation rate of the hypnagogic heart rate is scored at a second lowest point when the variation rate of the hypnagogic heart rate is ranged between "the average comparative value$+2\sigma$" and "the average comparative value$+3\sigma$". The variation rate of the hypnagogic heart rate is scored at a third lowest point when the variation rate of the hypnagogic heart rate is ranged between "the average comparative value$+\sigma$" and "the average comparative value$+2\sigma$". When the variation rate of the hypnagogic heart rate is smaller than "the average comparative value$+\sigma$", the variation rate of the hypnagogic heart rate is scored higher than the third lowest point.

Each of the scores of the hypnagogic heart rate, the variation of the hypnagogic heart rate, the duration time of body motion and the hypnagogic parasympathetic nerve activity value is assigned a corresponding weight described as each coefficient W1, W2, W3 and W4 respectively.

The easiness to get to sleep is scored by use of an equation 2.

Score of Easiness to Get to Sleep=$W1$×Score of Hypnagogic Heart Rate+$W2$×Score of Variation of Hypnagogic Heart Rate+$W3$×Score of Duration Time of Body Motion+$W4$×Score of Hypnagogic Parasympathetic Nerve Activity Value (Equation 2)

The wake-up-mood quality is evaluated based on at least one of a heart rate before a wake-up time, an variation rate of a heart rate (degree of increase of the heart rate) before the wake-up time, the parasympathetic nerve activity value before the wake-up time and a probability of a sleeping condition to be defined as a rapid eye movement (REM) sleep. The probability of the sleeping condition to be defined as the REM sleep is hereinafter described as a probability for the REM sleep. The probability for the REM sleep is determined based on the autonomic nerve activity or the body motion amount.

The autonomic nerve activity is indicated by a calculated value of "the sympathetic nerve activity÷the parasympathetic nerve activity". When the calculated value for the autonomic nerve activity is larger, the probability for the REM sleep becomes higher. Also, when the body motion amount is larger, the probability for the REM sleep becomes higher.

The wake-up-mood quality is evaluated as better when the heart rate before the wake-up time is larger, the variation rate of the heart rate is larger in increase (the degree of increase of the heart rate is larger) before the wake-up time, the probability for the REM sleep is higher, or the parasympathetic nerve activity value before the wake-up time is smaller. The wake-up-mood quality may be evaluated for a predetermined period before the wake-up time.

The heart rate before the wake-up time is scored based on an average comparative value of prestored heart rates before the wake-up time, which are stored in the storage device 23 as the base data. The heart rate before the wake-up time is scored at a maximum point when the heart rate before the wake-up time is larger than "the average comparative value$+3\sigma$". Also, the heart rate before the wake-up time is scored at the second highest point when the heart rate before the wake-up time is ranged between "the average comparative value$+2\sigma$" and "the average comparative value$+3\sigma$". The heart rate before the wake-up time is scored at the third highest point when the heart rate before the wake-up time is ranged between "the average comparative value$+\sigma$" and "the average comparative value$+2\sigma$". The heart rate before the wake-up time is scored less than the third highest point when the heart rate before the wake-up time is smaller than "the average comparative value$+\sigma$". The variation rate of the heart rate before the wake-up time is scored similarly to the heart rate before the wake-up time. The variation rate of the heart rate before the wake-up time is scored based on an average comparative value of the prestored variation rates of the heart rates in the storage device 23.

The parasympathetic nerve activity value before the wake-up time is scored based on an average comparative value of prestored parasympathetic nerve activity value before the wake-up time, which are stored in the storage device 23 as the base data. The parasympathetic nerve activity value before the wake-up time is scored at a maximum point when the parasympathetic nerve activity value is smaller than "the average comparative value−3σ". Also, the parasympathetic nerve activity value is scored at the second highest point when the parasympathetic nerve activity value is ranged between "the average comparative value−3σ" and "the average comparative value−2σ". The parasympathetic nerve activity value is scored at the third highest point when the parasympathetic nerve activity value is ranged between "the average comparative value−2σ" and "the average comparative value−σ". The parasympathetic nerve activity value is scored less than the third highest point when the parasympathetic nerve activity value is larger than "the average comparative value−σ".

The probability for the REM sleep is scored at the maximum when the probability of the sleeping condition to be defined as the REM sleep is 100%. The probability for the REM sleep is scored proportionally to the probability when the probability changes.

Each of the scores of the heart rate before the wake-up time, the variation rate of the heart rate before the wake-up time, the probability for the REM sleep and the parasympathetic nerve activity value before the wake-up time is assigned a corresponding weight described as each coefficient W1, W2, W3 and W4 respectively.

Thus, the wake-up-mood quality is scored by use of an equation 3.

Wake-up-mood quality=$W1 \times$Score of Heart Rate Before Wake-Up Time+$W2\times$Score of Variation Rate of Heart Rate Before Wake-Up Time+$W3\times$Score of Probability for REM Sleep+$W4\times$Score of Parasympathetic Nerve Activity Value Before Wake-Up Time (Equation 3)

The sleep habit is evaluated based on at least one of the bedtime, the wake-up time and sleep duration.

When the bedtime, the wake-up time and the sleep duration are regulated, the sleep habit is well evaluated. The bedtime is measured when the pulse wave sensor is turned on. The wake-up time is measured when the pulse wave sensor is turned off. The sleep duration is calculated based on each time, at which the pulse wave sensor is turned on or off.

The bedtime is scored based on an average comparative value of stored bedtime, which is stored in the storage device 23 as base data. The bedtime is scored at a maximum point when the bedtime is ranged between "the average comparative value±σ". Also, the bedtime is scored at the second highest point when the bedtime is ranged between "the average comparative value±2σ" but not between "the average comparative value±σ". The bedtime is scored at the third highest point when the bedtime is ranged between "the average comparative value±3σ" but not between "the average comparative value±2σ". The wake-up time and the sleep duration are scored similarly to the bedtime based on corresponding average comparative values of the prestored wake-up time and the stored sleep duration.

Each of the scores of the bedtime, the wake-up time and the sleep duration is assigned a corresponding weight described as a coefficient W1, W2 and W3 respectively. Thus, the sleep habit is scored by use of an equation 4.

Score of Sleep Habit = $W1\times$Score of Bedtime+$W2\times$Score of Wake-up Time+ $W3\times$Score of Sleep Duration (Equation 4)

The sleep normality is evaluated based on a coefficient of variation of a pulse interval (CVrr), a duration ratio of body motion for one night and a range (height or amplitude of variation) of sleep rhythm. The sleep rhythm is based on "sympathetic nerve activity÷parasympathetic nerve activity" or parasympathetic nerve activity.

When the CVrr is smaller, also when the duration ratio of the body motion in one night is smaller, also when the range of the sleep rhythm is larger, the sleep normality is evaluated as higher.

The CVrr is defined by an equation 5, and when the user is suffering from an irregular pulse or sleep apnea syndrome, a value of the CVrr is increased.

CVrr(%)=Standard Deviation of Instantaneous Pulse Interval at Arbitrary Time Period÷Average of Instantaneous Pulse Interval at Arbitrary Time Period×100 (Equation 5)

The sleep rhythm is shown by repetition of the REM and a non-rapid eye movement (NREM) phases of sleep, each of which has an approximately 90-minute interval. The range of the sleep rhythm is disclosed in Japanese Unexamined Patent Publication No. 2002-291710. Specifically, the range of the sleep rhythm is calculated based on a difference between maximum and minimum values of the parasympathetic nerve activity values for one night, or based on a difference between maximum and minimum values of the "sympathetic nerve activity÷parasympathetic nerve activity".

Returning to the second embodiment of the present invention, when a value of the CVrr at the NREM phase of sleep is larger than a predetermined threshold value (X) %, the CVrr is scored less.

The duration ratio of the body motion for one night is scored based on an average comparative value of prestored ratios of duration of the body motion, which are stored in the storage device 23 as the base data. The duration ratio of the body motion is scored at a maximum point when the duration ratio of the body motion is smaller than "the average comparative value−3σ". Also, the duration ratio of the body motion is scored at the second highest point when the duration ratio of the body motion is ranged between "the average comparative value−3σ" and "the average comparative value−2σ". The duration ratio of the body motion is scored at the third highest point when the duration ratio of the body motion is ranged between "the average comparative value−2σ" and "the average comparative value−σ". The duration ratio of the body motion is scored less than the third highest point when the duration ratio of the body motion is larger than "the average comparative value−σ".

The range of sleep rhythm is scored based on an average comparative value of prestored ranges of sleep rhythm, which are stored in the storage device 23 as the base data. The range of sleep rhythm is scored at a maximum point when the range of sleep rhythm is larger than "the average comparative value+3σ". Also, the range of sleep rhythm is scored at the second highest point when the range of sleep rhythm is ranged between "the average comparative value+2σ" and "the average comparative value+3σ". The range of sleep rhythm is scored at the third highest point when the range of sleep rhythm is ranged between "the average comparative value+σ" and "the average comparative value+2σ". The range of sleep rhythm is scored less than the third highest point when the range of sleep rhythm is smaller than "the average comparative value+σ".

Each of the scores of the CVrr, the duration ratio of body motion for one night and the range of sleep rhythm is assigned a corresponding weight by described as each coefficient W1, W2 and W3 respectively.

Thus, the sleep normality is scored by use of an equation 6.

$$\text{Score of Sleep normality} = W1 \times \text{Score of } CVrr + \\ W2 \times \text{Score of Duration ratio of Body Motion} + \\ W3 \times \text{Score of Range of Sleep Rhythm} \quad \text{(Equation 6)}$$

Total value is scored based on the above evaluation categories.

For example, each score of the evaluation categories is assigned a corresponding weight (W1 to W5) and a total score is calculated by use of an equation 7.

$$\text{Total Score} = W1 \times \text{Score of Sleep Quality} + \\ W2 \times \text{Score of Easiness of Get to Sleep} + \\ W3 \times \text{Score of Wake-Up-Mood Quality} + \\ W4 \times \text{Score of Sleep Habit} + \\ W5 \times \text{Score of Sleep Normality} \quad \text{(Equation 7)}$$

In the present embodiment, the evaluation categories, such as the sleep quality, are calculated and evaluation results are displayed. Therefore, information, which are necessary for preferable sleep can be provided easily and certainly.

Also, in the present embodiment, causes for degrading the sleep quality can be displayed. Thus, the high quality sleep can be achieved when the causes are appropriately dealt with. Poorly scored one of the evaluation categories except for the sleep quality may be defined as a cause of degrading the parasympathetic nerve activity (sleep quality). The poorly scored one may be displayed as the cause. Thus, the cause may be appropriately dealt with.

Further, in the present embodiment, the total score is displayed. Thus, the sleep can be more accurately evaluated by eliminating the external effects, such as a length of daily sleep duration.

The present invention is not limited to the above embodiments. Various modifications can be applied for the present invention if the modifications do not deviate from the present invention.

For example, in the second embodiment, the sleep quality is evaluated based on human body information supplied by the pulse wave sensor of the sleep information processing apparatus. However, alternative sensors, such as an electrocardiograph may be used.

Also, the controlling apparatus for the pulse wave sensor may process the measured data for evaluating the sleep quality. However, firstly the measured data may be stored in a memory and then the measured data may be transmitted in bulk to a computer or a mobile phone, where the measured data may be batched. The recommended bedtime may be announced based on alternative sleep-affecting life activity, such as smoking or bathing, in addition to drinking the alcohol or taking the exercise.

Additional advantages and modifications will readily occur to those skilled in the art. The invention in its broader terms is therefore not limited to the specific details, representative apparatus, and illustrative examples shown and described.

What is claimed is:

1. A sleep information processing apparatus for evaluating a sleep feature of a user comprising:
    a sensing means for sensing pulse wave data of the user;
    a storage means for storing at least one relation information set, which indicates a relationship between model pulse wave data and corresponding sleep feature data, wherein the corresponding sleep feature data indicates a corresponding predetermined sleep feature;
    a sleep evaluating means for evaluating the corresponding predetermined sleep feature based on the sensed pulse wave data of the user and the at least one relation information set; and
    a notifying means for notifying evaluation result data to the user based on the evaluated corresponding predetermined sleep feature, wherein
    when the corresponding predetermined sleep feature includes wake-up-mood quality, the relationship indicated by the at least one relation information set is determined in view of at least one of the following corresponding sleep feature data: a heart rate before a wake-up time, a variation rate of a heart rate before the wake-up time, a parasympathetic nerve activity value before the wake-up time, and a probability of a sleeping condition to be defined as a rapid eye movement sleep.

2. The sleep information processing apparatus according to claim 1, further comprising:
    an analyzing means for determining whether the evaluated corresponding predetermined sleep feature dissatisfies a predetermined condition; and
    a cause estimating means for estimating a cause that makes the evaluated corresponding predetermined sleep feature dissatisfy the predetermined condition when the analyzing means determines that the evaluated corresponding predetermined sleep feature dissatisfies the predetermined condition, wherein
    the notifying means notifies the cause, as the evaluation result data, to the user.

3. The sleep information processing apparatus according to claim 2, wherein:
    the at least one relation information set includes a plurality of relation information sets, each of which indicates the relationship between the model pulse wave data and the corresponding sleep feature data; and
    the corresponding sleep feature data indicates the corresponding predetermined sleep feature.

4. The sleep information processing apparatus according to claim 3, wherein:
    the sleep evaluating means scores each corresponding predetermined sleep feature, which corresponds to one of the plurality of relation information sets, to evaluate the corresponding predetermined sleep feature; and
    the notifying means notifies a score of each corresponding predetermined sleep feature, as the evaluation result data, to the user.

5. The sleep information processing apparatus according to claim 4, wherein
    the analyzing means determines that the evaluated corresponding predetermined sleep feature dissatisfies the predetermined condition when the score of the evaluated corresponding predetermined sleep feature is lower than a corresponding predetermined value.

6. The sleep information processing apparatus according to claim 3, wherein:
the sleep evaluating means assigns a weight to each corresponding predetermined sleep feature, which corresponds to one of the plurality of relation information sets, and scores each corresponding predetermined sleep feature to evaluate each corresponding predetermined sleep feature in such a manner that the sleep evaluating means calculates a total score of the sleep feature of the user by summing a weighted score of each corresponding predetermined sleep feature; and
the notifying means notifies the total score, as the evaluation result data, to the user.

7. The sleep information processing apparatus according to claim 1, wherein:
the at least one relation information set includes a plurality of relation information sets, each of which indicates the relationship between the model pulse wave data and the corresponding sleep feature data; and
the corresponding sleep feature data indicates the corresponding predetermined sleep feature.

8. The sleep information processing apparatus according to claim 7, wherein
each corresponding predetermined sleep feature, which corresponds to one of the plurality of relation information sets, includes corresponding one of at least one of sleep quality, easiness to get to sleep, the wake-up-mood quality, sleep habit, and sleep normality.

9. The sleep information processing apparatus according to claim 8, wherein
each corresponding predetermined sleep feature, which corresponds to one of the plurality of relation information sets, includes corresponding one of at least one of the easiness to get to sleep, the wake-up-mood quality, the sleep habit, and the sleep normality.

10. The sleep information processing apparatus according to claim 8, wherein
the relationship between the model pulse wave data and the corresponding sleep feature data, which indicates the corresponding predetermined sleep feature, is determined in view of corresponding sleep feature evaluation data.

11. The sleep information processing apparatus according to claim 10, wherein
when the corresponding predetermined sleep feature includes the sleep quality, the corresponding sleep feature evaluation data includes autonomic nerve activity data, which is calculated based on a heart rate fluctuation analysis and indicates a condition of an autonomic nerve activity.

12. The sleep information processing apparatus according to claim 10, wherein
when the corresponding predetermined sleep feature includes the easiness to get to sleep, the corresponding sleep feature evaluation data includes at least one of a hypnagogic heart rate, a variation rate of the hypnagogic heart rate, a duration time of body motion, and a hypnagogic parasympathetic nerve activity value, which indicates a condition of a hypnagogic parasympathetic nerve activity.

13. The sleep information processing apparatus according to claim 10, wherein
when the corresponding predetermined sleep feature includes the sleep habit, the corresponding sleep feature evaluation data includes at least one of a bedtime, a wake-up time and sleep duration.

14. The sleep information processing apparatus according to claim 10, wherein
when the corresponding predetermined sleep feature includes the sleep normality, the corresponding sleep feature evaluation data includes at least one of a coefficient of variation of a pulse interval, a duration ratio of body motion for one night, and an amplitude of variation of sleep rhythm.

15. The sleep information processing apparatus according to claim 8, wherein
when the corresponding predetermined sleep feature includes one of the sleep quality and the wake-up-mood quality, the corresponding sleep feature evaluation data includes at least one of the followings:
a parasympathetic nerve activity value, which indicates a condition of a parasympathetic nerve activity;
a ratio of a sympathetic nerve activity value, which indicates a condition of a sympathetic nerve activity, to the corresponding parasympathetic nerve activity value;
body motion of the user; and
a variation rate of a heart rate.

16. The sleep information processing apparatus according to claim 1, wherein:
the sleep evaluating means scores each corresponding predetermined sleep feature, which corresponds to one of the at least one relation information set, to evaluate the corresponding predetermined sleep feature; and
the notifying means notifies a score of each corresponding predetermined sleep feature, as the evaluation result data, to the user.

17. The sleep information processing apparatus according to claim 1, wherein
the at least one relation information set, which is stored in the storage means, is prepared in relation to at least one of the followings:
the user;
people of a same generation with the user; and
people of a same gender with the user.

18. The sleep information processing apparatus according to claim 1, wherein
the sleep information processing apparatus is a biosensor.

19. The sleep information processing apparatus according to claim 1, wherein
the sleep information processing apparatus is a pulse wave sensor.

20. A non-transitory computer readable storage medium that stores a computer program for processing sleep information, the computer program comprising:
a code segment configured to direct a sensing means to sense pulse wave of a user;
a code segment configured to direct a storage means to store at least one relation information set, the at least one relation information set indicating a relationship between model pulse wave data and corresponding sleep feature data, wherein the corresponding sleep feature data indicates a corresponding predetermined sleep feature;
a code segment configured to direct an evaluation means to evaluate each corresponding predetermined sleep feature based on the sensed pulse wave data of the user and a corresponding one of the at least one relation information set; and a code segment configured to direct a notifying means to notify evaluation result data to the user based on the evaluated corresponding predetermined sleep feature, wherein when the corresponding predetermined sleep feature includes wake-up-mood quality, the relationship indicated by the at least one relation information set is determined in view of at least one of the following corresponding sleep feature data: a heart rate before a wake-up time, a variation rate of a heart rate before the wake-up time, a parasympathetic nerve activity value before the wake-up time, and a probability of a sleeping condition to be defined as a rapid eye movement sleep.

21. A sleep information processing apparatus for evaluating a sleep feature of a user comprising:

a sensing means for sensing pulse wave data of the user;

a storage means for storing at least one relation information set, which indicates a relationship between model pulse wave data and corresponding sleep feature data, wherein the corresponding sleep feature data indicates a corresponding predetermined sleep feature;

a sleep evaluating means for evaluating the corresponding predetermined sleep feature based on the sensed pulse wave data of the user and the at least one relation information set; and a notifying means for notifying evaluation result data to the user based on the evaluated corresponding predetermined sleep feature, wherein the at least one relation information set includes a plurality of relation information sets, each of which indicates the relationship between the model pulse wave data and the corresponding sleep feature data;

the corresponding sleep feature data indicates the corresponding predetermined sleep feature;

each corresponding predetermined sleep feature, which corresponds to one of the plurality of relation information sets, includes corresponding one of at least one of sleep quality, easiness to get to sleep, the wake-up-mood quality, sleep habit, and sleep normality;

the relationship between the model pulse wave data and the corresponding sleep feature data, which indicates the corresponding predetermined sleep feature, is determined in view of corresponding sleep feature evaluation data; and when the corresponding predetermined sleep feature includes the wake-up-mood quality, the corresponding sleep feature evaluation data includes at least one of a heart rate before a wake-up time, a variation rate of a heart rate before the wake-up time, a parasympathetic nerve activity value before the wake-up time and a probability of a sleeping condition to be defined as a rapid eye movement sleep.

* * * * *